US011906507B2

(12) United States Patent
Wei et al.

(10) Patent No.: US 11,906,507 B2
(45) Date of Patent: Feb. 20, 2024

(54) METHODS FOR TESTING SKIN SAMPLES

(71) Applicant: The Procter & Gamble Company, Cincinnati, OH (US)

(72) Inventors: Karl Shiqing Wei, Mason, OH (US); Feng Yue, Beijing (CN); Hechuan Yu, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 239 days.

(21) Appl. No.: 17/210,957

(22) Filed: Mar. 24, 2021

(65) Prior Publication Data

US 2021/0302408 A1 Sep. 30, 2021

(30) Foreign Application Priority Data

Mar. 24, 2020 (WO) ................ PCT/CN2020/080789

(51) Int. Cl.
*G01N 33/483* (2006.01)
*G01N 33/569* (2006.01)

(52) U.S. Cl.
CPC ... *G01N 33/4833* (2013.01); *G01N 33/56916* (2013.01); *G01N 33/56938* (2013.01); *G01N 33/56961* (2013.01); *G01N 33/56983* (2013.01)

(58) Field of Classification Search
CPC ......... G01N 33/4833; G01N 33/56916; G01N 33/56938; G01N 33/56961; G01N 33/56983; G01N 33/50
See application file for complete search history.

(56) References Cited

U.S. PATENT DOCUMENTS

| | | | |
|---|---|---|---|
| 6,110,908 A | 8/2000 | Guthery | |
| 6,210,695 B1 | 4/2001 | Beerse et al. | |
| 6,624,126 B1 | 9/2003 | Kasuga et al. | |
| 8,119,168 B2 | 2/2012 | Johnson et al. | |
| 8,685,908 B2 | 4/2014 | Smith, III et al. | |
| 8,795,695 B2 | 8/2014 | Smith, III et al. | |
| 8,796,252 B2 | 8/2014 | Rioux et al. | |
| 9,333,157 B2 | 5/2016 | Jiang et al. | |
| 9,504,638 B2 | 11/2016 | Smith, III et al. | |
| 9,655,831 B2 | 5/2017 | Jiang et al. | |
| 9,750,674 B2 | 9/2017 | Wei et al. | |
| 9,901,584 B2 | 2/2018 | Wei et al. | |
| 10,183,298 B2 | 1/2019 | Walling et al. | |
| 10,201,481 B2 | 2/2019 | Smith, III et al. | |
| 10,232,047 B2 | 3/2019 | Prasad et al. | |
| 10,450,537 B2 | 10/2019 | Salvador et al. | |
| 10,688,117 B2 | 6/2020 | Nadau Fourcade | |
| 2002/0168327 A1 | 11/2002 | Bailey et al. | |
| 2003/0068289 A1 | 4/2003 | Bailey et al. | |
| 2004/0092415 A1 | 5/2004 | Focht et al. | |
| 2004/0241099 A1 | 12/2004 | Popp et al. | |
| 2005/0008606 A1 | 1/2005 | Pawson et al. | |
| 2005/0118276 A1 | 6/2005 | Lei et al. | |
| 2006/0182708 A1 | 8/2006 | Bockmuhl et al. | |
| 2007/0190004 A1 | 8/2007 | Bockmuhl et al. | |
| 2009/0028626 A1 | 1/2009 | Hokimoto et al. | |
| 2009/0169644 A1 | 7/2009 | Goddinger et al. | |
| 2010/0086520 A1 | 4/2010 | Reindl et al. | |
| 2011/0277796 A1 | 11/2011 | Walters et al. | |
| 2012/0128777 A1 | 5/2012 | Keck et al. | |
| 2012/0219610 A1 | 8/2012 | Smith, III et al. | |
| 2013/0045248 A1 | 2/2013 | Coffindaffer et al. | |
| 2013/0045263 A1 | 2/2013 | Smith, III et al. | |
| 2013/0045284 A1 | 2/2013 | Stella | |
| 2013/0045285 A1 | 2/2013 | Stella et al. | |
| 2013/0045907 A1 | 2/2013 | Lanzalaco et al. | |
| 2013/0045961 A1 | 2/2013 | Smith, III et al. | |
| 2014/0303135 A1 | 10/2014 | Smith, III et al. | |
| 2014/0335040 A1 | 11/2014 | Yu et al. | |
| 2015/0196477 A1 | 7/2015 | Stark et al. | |
| 2015/0250697 A1 | 9/2015 | Smith, III et al. | |
| 2015/0251222 A1 | 9/2015 | Walling et al. | |
| 2016/0074300 A1 | 3/2016 | Salvador et al. | |
| 2016/0128944 A1 | 5/2016 | Chawrai | |
| 2016/0215326 A1 | 7/2016 | Martin et al. | |
| 2016/0262399 A1 | 9/2016 | Smith, III et al. | |
| 2020/0289525 A1 | 9/2020 | Wei et al. | |

FOREIGN PATENT DOCUMENTS

| | | | |
|---|---|---|---|
| CN | 1795383 A | 6/2006 | |
| CN | 101690697 A | 4/2010 | |
| CN | 104095766 A | 10/2014 | |
| CN | 106932329 A | 7/2017 | |
| CN | 110806408 A | 2/2020 | |
| FR | 2685638 B1 | 4/1995 | |
| WO | 2008086596 A1 | 7/2008 | |

(Continued)

OTHER PUBLICATIONS

Pierard-Franchimont 2006 (Activity of the Triazole Antifungal R126638 as Assessed by Corneofungimetry; Skin Pharmacol. Physiol. 200619:50-56) (Year: 2006).*
Barnetson et al. 1973 (Skin sampling for Candida with adhesive tape; British Journal of Dermatology 88:487). (Year: 1973).*
Griffeth et al. 2012 (Optimization of a *Staphylococcus aureus* adhesion assay for equine corneocytes; Vet. Dermatol. 23(1): 57-e13). (Year: 2012).*
Pierard 1997 (Povidone-iodine wash solutions in the prevention of superficial fungal infections; predictive evaluation using the corneofungimetry bioassay; Eur J Clin Pharmacol 53:101-104). (Year: 1997).*
Simou et al. 2005 (Adherence of *Staphylococcus intermedius* to corneocytes of healthy and atopic dogs: effect of pyoderma, pruritus score, treatment and gender; Veterinary Dermatology 16: 385-391) (Year: 2005).*
Waldman et al. 1996 (Human enterovirus infection in stray dogs. Some Aspects of interest to public health; Rev. Inst. Med. Trop. Sao Paulo 38(2):157-161) (Year: 1996).*

(Continued)

*Primary Examiner* — Brian Gangle
*Assistant Examiner* — Lakia J Jackson-Tongue
(74) *Attorney, Agent, or Firm* — Alexandra S. Anoff

(57) ABSTRACT

A method of taking a skin sample can include placing an adhesive onto a portion of skin and lifting the adhesive from the skin. A skin sample may then be tested while still on the adhesive, for example, by inoculating the sample with a bacterium, fungus, virus, or a combination.

17 Claims, 3 Drawing Sheets

(56) References Cited

FOREIGN PATENT DOCUMENTS

| WO | 2010111374 A2 | 9/2010 | |
|---|---|---|---|
| WO | 2014025290 A1 | 2/2014 | |
| WO | WO-2016198535 A1 * | 12/2016 | ........... G01N 33/502 |
| WO | 2018049556 A1 | 3/2018 | |
| WO | 2018049557 A1 | 3/2018 | |
| WO | 2018049558 A1 | 3/2018 | |
| WO | 2018050056 A1 | 3/2018 | |
| WO | 2018161062 A1 | 9/2018 | |
| WO | 2020035707 A1 | 2/2020 | |

OTHER PUBLICATIONS

Lademann et al. 2009 (The tape stripping procedure—evaluation of some critical parameters; European Journal of Pharmaceutics and Biopharmaceutics 72: 317-323) (Year: 2009).*
R. St C. Barnetson et al. "Skin sampling for Candida with adhesive tape" British Journal of Dermatology, vol. 88, No. 5, May 31, 1973 (May 31, 1973),pp. 487-491.
Zhang Lei et al. "The technology of pasting stratum corneum and its application" Chinese Journal of Aesthetic Medicine, vol. 21, No. 5, May 31, 2012 (May 31, 2012),pp. 873-875.
PCT Search Report and Written Opinion for PCT/CN2020/080789 dated Dec. 30, 2020, 9 pages.
All Office Actions; U.S. Appl. No. 16/352,413, filed Mar. 13, 2019.
Database GNPD [Online] MINTEL; Feb. 2016 (Feb. 2016), "Conditioner", XP002781916, Database Accession No. 3821933 *the whole document*, 2 pgs.
Griffeth et al. "Optimization of a *Staphylococcus aureus* Adhesion Assay for Equine Corneocytes" In Journal of Veterinary Dermatology, vol. 23, No. 1, Feb. 28, 2012, pp. 1-8.
Hara et al., Suppression of Microbial Metabolic Pathways Inhibits the Generation of the Human Body Odor Component Diacetyl by *Staphylococcus* spp, Nov. 2014, pp. 1-13, PLoS One.
Increased scalp skin lipids in response to antidandruff treatment containing zinc pyrithione (Unilever), Archives of Dermatological Research (2003), vol. 295, issue 3, pp. 127-129. Patients had dandruff.
Kong, et al., "Temporal shifts in the skin microbiome associated with disease flares and treatment in children with atopic dermatitis", Genome Research, Published by Cold Spring Harbor Laboratory Press, 2012, vol. 22, pp. 850-859.
McEwan et al. "Monosaccharide Inhibition of Adherence by Pseudomonas Aeruginosa to Canine Corneocytes" In Journal of Veterinary Dermatology, vol. 19, No. 4, pp. 221-225, Jul. 8, 2008.
Microbiome of affected and unaffected skin of patients with atopic dermatitis before and after emollient treatment, J. of Drugs in Dermatology, 13(11), pp. 1365-1372, 2014.
Piérard-Franchimont et al. "Activity of the Triazole Antifungal R126638 as Assessed by Corneofungimetry" In Journal of Skin Pharmacology and Physiology, vol. 19, No. 1, Oct. 20, 2005, pp. 50-56.
Simou et al. "Adherence of *Staphylococcus intermedius* to Corneocytes of Healthy and Atopic Dogs: Effect of Pyoderma, Pruritus Score, Treatment and Gender" In Journal of Veterinary Dermatology, vol. 16, No. 6,pp. 385-391, Nov. 30, 2005.
Stratum corneum dysfunction in dandruff ( Unilever), International J. Cosmetic science (2012), vol. 34, issue 4, pp. 298-306.
The skin microbiome in atopic dermatitis and its relationship to emollients, J. of Cutaneous Medicine and Surgery, 20(1), 2015, 8 pgs.
Wang Shan et al. "The Update Progress of relationship between Skin Microbiome and Atopic Dermatitis," China Medical Abstract of Dermatology, vol. 33, No. 2, Apr. 30, 2016 (Apr. 30, 2016),,lines 1-4 of right column, lines 28-34 of left column, p. 125.
Ward L. Billhimer, et al. "A modified cup scrub method for assessing the antibacterial substantivity of personal cleansing products" Aug. 15, 2001, pp. 369-275.
Williams et al., The Role of the Skin Microbiome in Atopic Dermatitis, Curr Allergy Asthma Rep (2015) 15: 65, 10 pages.
Zinc monoglycerolate. A slow release source of therapeutic zinc; solubilization by endogenous ligands. Agents and Actions (1992), vol. 36, issue1-2, pp. 152-158.

* cited by examiner

METHODS FOR TESTING SKIN SAMPLES

FIELD OF THE INVENTION

The present application is directed to methods of testing skin samples and methods of testing skin products.

BACKGROUND OF THE INVENTION

The skin is the body's largest organ and is part of the body's natural defense to microbial attack. The natural skin defense is made up of a multitude of components. For example, the skin's natural defense includes the skin's ability to be a physical barrier, the pH of the skin, the skin microbiome, lipids on the skin, chemical components of the skin, etc.

The skin's ability to provide a natural defense against microbial attack can be impacted by things with which it comes into contact during the day, like skin products. To this point, testing of the skin's natural defense has primarily focused on the microbiome. As noted, however, this is only one aspect of the skin's natural defense system. In addition, testing of the microbiome is often done by removing a skin sample, isolating the molecule of interest from the sample, and then quantifying the molecule of interest. Removing the target molecule from its natural environment, however, could have unintended consequences on the results and can also prevent an understanding of the impact to more than one component of the skin's natural defense and/or the potential impact of the skin's natural defense mechanism to the information being collected. In addition, the isolation of the target molecules from the original sample can be costly and time consuming. As such, there is a need for a new method to evaluate skin samples.

SUMMARY OF THE INVENTION

A method for testing a skin sample, includes: a) obtaining a sample of skin cells from a target area, wherein the skin cells are obtained with the application and removal of an adhesive; b) applying a bacterial load, fungal load, viral load, or a combination thereof, to the sample on the adhesive; and c) measuring a bacterial level, fungal level, viral level, or a combination thereof, of the sample.

A method for testing a skin product, includes: a. applying a skin product to a target area; b. optionally, rinsing the skin product from the target area; c. obtaining a sample of skin cells from the target area, wherein the skin cells are obtained with the application and removal of an adhesive; d. applying a bacterial load, fungal load, viral load, or a combination thereof, to the sample on the adhesive; and e. measuring a bacterial level, fungal level, viral level, or a combination thereof, of the sample.

These and other expressions of the invention will be discussed more fully below.

DETAILED DESCRIPTION OF THE INVENTION

Figure 1:
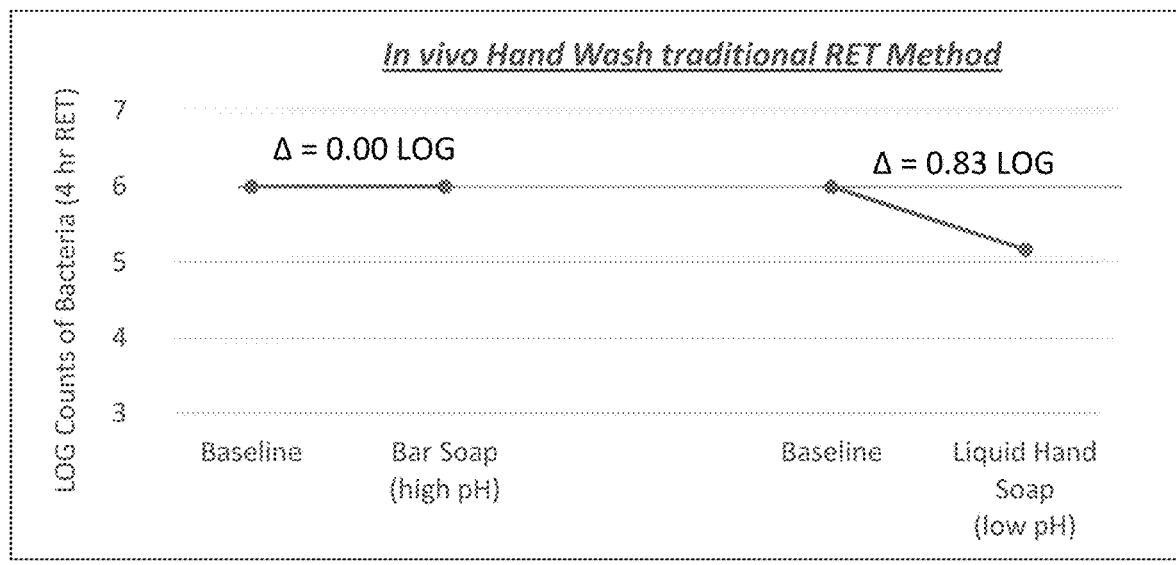
FIG. 1 is a graph showing the log counts of bacteria after washing with a bar soap chassis and a liquid hand soap chassis utilizing a standard residual efficacy test method.

Product testing before putting a product on the market is important. Testing of a product allows the developer to understand whether, for example, the product is performing as expected and whether there is consumer acceptance of the product. When products are made for application to the human body, the types of testing that can be done for a product can be limited and/or expensive as the need for human subjects and requirements for safety of those subjects are paramount.

Due to timing and cost constraints, it is advantageous to be able to assess efficacy of formulations in a quick and cost relevant way. Previously these quick and less costly tests included things like skin mimics or explanted human skin. A skin mimic is an artificial material made to resemble skin. However, while beneficial for initial screening of things like deposition of an ingredient onto the skin and/or lather during cleansing; it lacks the underlying biology of true skin. Thus, there can be a discrepancy in what is seen on a skin mimic and what is observed on actual human skin. Also, the inability of a skin mimic to be used for testing of any impact of a product on one or more of the skin's natural defense components or the ability to understand if the skin's natural defense components are influencing any testing are further detractors from the use of skin mimic.

Another substitute for direct testing on humans is the use of explant skin. Explant skin is skin that is removed during surgery and no longer needed. Explant skin has a few major downfalls. First, explant skin is only viable for a very short period of time making the timing of shipping, receiving, and testing a very confined window. Second, the supply of explant skin can be unpredictable. Moreover, skin explants are laborious to maintain even though they have only a short shelf life. All of these make skin explant less than ideal. Similar issues can be seen with a skin biopsy.

For direct testing on humans, product is applied directly on a target site of the skin. Depending on the type of testing being conducted, the application of the product may be followed with the inoculation of the test site with a bacteria and/or fungus. When these materials are inoculated on the skin, they are often covered with an occlusive patch to help prevent the unintended transfer of the inoculated material to other areas of the skin. There are inherent risks in inoculating a bacteria and/or fungus directly onto the skin of a user. Given this risk to the subject, there are strict requirements for these types of tests which are both costly and timely.

Once the target site is ready for sample collection, researchers can take a skin sample by, for example, rubbing a swab over the skin, using an adhesive to lift a skin sample, or placing a cylinder over the area of the skin and utilizing special fluids and mechanical agitation. While the collection procedures are not invasive like some of the ones above, the target material is trapped in the collection implement or in the liquids used during the collection process and often needs to be removed before analysis. This is regularly done by using an extraction procedure. Extraction can be accomplished utilizing rinses, extraction buffers, etc. The need to isolate the material from the collection implement or liquid requires additional time before analysis can be performed.

There can also be a partial loss of target material due to incomplete or inefficient extraction methods.

The target materials then may need to be separated from the extraction materials before they can be analyzed requiring even more time. The addition of liquids to the samples and the loss of some of the materials during the extraction and/or isolation processes can create limitations regarding analytical sensitivity. Moreover, the target materials have been removed from their natural skin environment via the extraction process. Without the intact natural skin defense components, it is unclear how/if these elements are contributing to the results. This is especially true where the researcher is investigating antimicrobial efficacy.

The present inventors have discovered that a skin sample taken with an adhesive can be utilized directly on the adhesive. This means, for example, that the skin sample on the strip can be inoculated on the strip removing the need to inoculate directly on the skin of a panelist prior to taking the skin sample. In addition, with at least some testing methods, the sample on the strip can be used without the need to remove materials from the adhesive or to remove any backing material on the adhesive prior to testing. So, the skin sample on the adhesive may be placed, for example, into a testing apparatus or even cut into pieces and placed in a testing apparatus.

To show that a skin sample on an adhesive could be utilized to similar effect as a traditional direct panelist inoculation and extraction method, the results from a traditional residual efficacy test clinical ("traditional RET method") and a new method inoculating the skin sample on the adhesive were compared ("NET method"). The residual efficacy test looks at the antimicrobial effect of a bar soap chassis (bar soap) and a liquid hand soap chassis (LHS), neither of which contain a traditional antimicrobial active.

For the traditional RET method, a randomized, placebo controlled, and double-blind study is followed utilizing a residual efficacy protocol. Panelists are subjected to a 7-14 day wash out period where they are asked to avoid any products with anti-bacterial efficacy until the trial is complete. After the wash out period, each panelist visits a designated site where a forearm is washed with a target product 3 times at one hour intervals. During the wash, the volar surface of the forearm and the target product are wetted under running tap water maintained at 95° C. to 100° C. The bar is rubbed in an up and down motion from wrist to elbow for 15 seconds. For the liquid hand soap, 0.7 mL of the hand soap is placed on the volar surface of the arm and spread evenly for 15 seconds. The lather is then rubbed on the forearm using the same motion for another 45 seconds. The arm is then rinsed for 15 seconds and patted dry with a paper towel.

After the third wash on the third day of washing, one area for germ inoculation is marked on the forearm. That area is inoculated with $10^5$ to $10^6$ colony forming units (CFU's) of *Staphylococcus aureus* (ATCC 27217) and occluded with an occlusive chamber patch. About 5 hours after occlusion, the patch is removed, and the bacteria harvested using a cup scrub technique. Then, each test area is disinfected using 75% ethanol and antibiotics immediately and reexamined 2 to 3 days later.

For a cup scrub method of harvesting, a rigid cylinder is placed against a target area of skin, here the portion of skin that was inoculated unless it is a control area. The cylinder is pressed against the skin with enough pressure to form a liquid tight seal. A recovery liquid is placed inside the cylinder in contact with the skin. The skin is then scrubbed with an appropriate implement, like a glass or rubber rod. The liquid is then removed from the cylinder and manipulated as appropriate for the desired testing. For example, the harvested bacteria are diluted, plated, and incubated for about 48 hours, then counted (CFU). The American Standard Test Method for a sup scrub procedure is ASTM E1874-14. A detailed description of an exemplary residual efficacy test method is included in Billhimer, Berge, Englehart, Rains, and Keswick, "A modified cup scrub method for assessing the antibacterial substantivity of personal cleansing products," J. Cosmet. Sci., 52, 369-375 (2001).

As can be seen from FIG. 1, the traditional RET results showed the bar soap chassis had no measurable residual efficacy against *S. Aureus* whereas the liquid hand soap chassis showed a significant innate defense property against *S. Aureus*.

Figure 2:
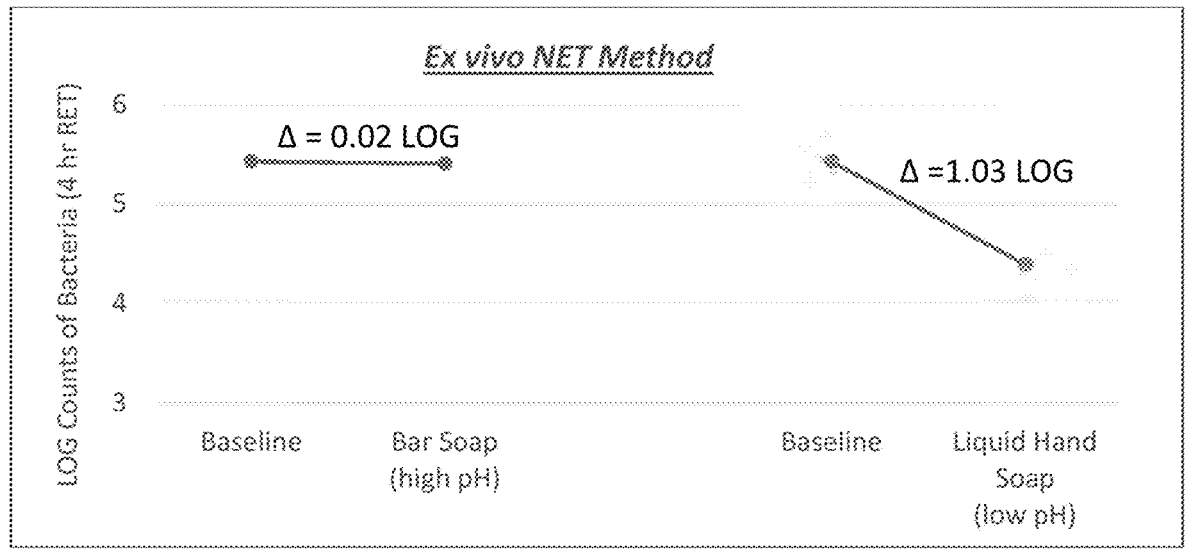
FIG. 2 is a graph depicting the log counts of bacteria after washing with a bar soap chassis and a liquid hand soap chassis utilizing a skin sample on an adhesive.

The same chassis were tested utilizing the new NET method of inoculating the skin sample directly on the adhesive. For the NET method, a skin sample was taken with an adhesive after a washing and rinsing protocol as described above for the traditional RET. The skin sample on the adhesive strip was then inoculated with *S. Aureus*, also as noted above for the traditional RET. The adhesive is placed on a trypticase soy agar plate with the skin sample side up. The inoculated sample is then reviewed for the growth of a bacteria and/or fungus over time. This is done utilizing an optical detection method, the Soleris® system. The results are then plotted on a graph showing the difference from baseline (before treatment) and from a sample taken 4 hours after treatment. As can be seen in FIG. 2, the new method showed the same trend as the traditional method of FIG. 1. Additional details about the NET method are described below in the Skin Sample Testing section.

The new method is faster and cheaper due, at least in part, to the elimination of the need to inoculate bacteria and/or fungus directly on the skin. It also allows, if desired, the sample to be used on the adhesive without extraction. Moreover, the ability to inoculate the skin sample on the adhesive also presents a safety advantage. Previously, bacteria and/or fungal samples were placed directly on the skin of a panelist. By removing the need for application of the bacteria and/or fungus to the skin of the panelist, any risk with having to do this is removed. It also allows for testing against a wider range bacteria and/or fungus as some of these materials were not able to be placed directly on the skin. Moreover, it allows panelists to leave after removal of the skin sample with the adhesive where they previous would have been required to stay an additional 5 hours to complete the inoculation and collection period. This change could make it easier to recruit panelists and could require less payment to panelists since much less of their time is required.

The ability to inoculate samples directly on an adhesive also contributes to the robustness of the test. Normally, only 3 samples are taken from one arm test site due at least in part to the need to adequately space samples for inoculation and occlusive coverage. Inoculating the skin samples directly on the adhesive allows for more samples to be taken from a sampling site. This increases the robustness of the testing. The ability to take more samples from a site also allows for a higher throughput and, thus, faster cycling of testing for products.

Additional advantages come from the ability to test the sample directly on the adhesive. As noted above, there are many drawbacks from the procedures utilized to extract the skin sample or at least the target material from the adhesive. These are eliminated or at least minimized when the entire adhesive including the skin sample is used for testing.

Figure 3:
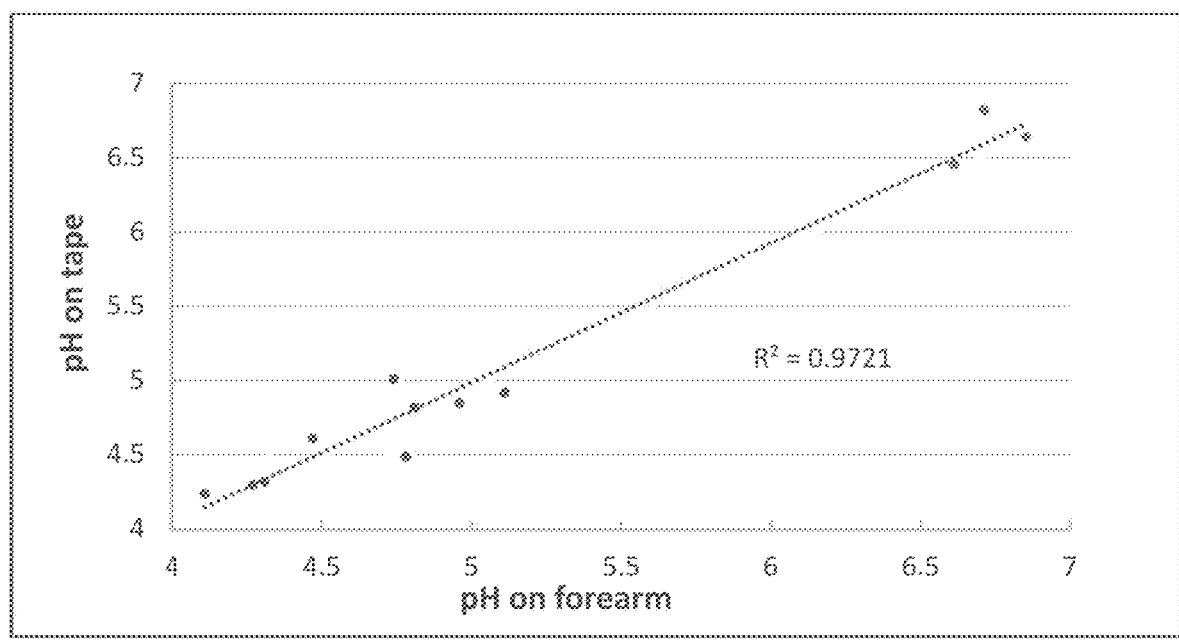
FIG. 3 is a graph depicting the pH on a subject's arm versus the pH on the surface of a tape strip after removal of skin sample on the subject's arm.

Moreover, testing on a skin sample while still on the adhesive showed the skin sample is in a more natural state. For example, the skin corneocytes on the adhesive tape strips maintain the same pH as the skin surface sampled (see FIG. 3). Thus, one can use an adhesive sampling method, like a tape strip, after application of a product to the skin to determine whether the application of the product impacted the pH of the treated area of skin. This allows for the determination of whether the product is impacting the skin's pH, and thus, impacting the skin's natural defense.

In addition to being able to understand the impact from a pH perspective, it is believed the skin sample lifted on an adhesive has a representative sample of at least some of the components of the skin's natural defense system as well. This allows for any product application to be evaluated in a more natural skin environment. This can be important, for example, when trying to understand whether a product impacts the skin's natural ability to protect itself or whether a product has an antimicrobial effect on skin. The test can also be used to understand the differences in natural skin defense from one person to another. Once a skin sample is taken and inoculated with a bacteria and/or fungus the growth rate of the bacteria and/or fungus can be measured. This will give the researcher an understanding of the skin's natural ability to repel an invasion by the selected bacteria and/or fungus.

Going further, the researcher can apply a product to the same area of skin, take a sample of the skin with an adhesive, inoculate the sample with the same bacteria and/or fungus, and measure the growth of the bacteria and/or fungus. The results can then be compared to those of the original skin sample to determine the impact of the product on the skin's natural defense. The results can also be compared at different time points to understand the impact over time and over different numbers of applications. In addition, the results can be used to determine if a tested product provides any antimicrobial and/or antifungal benefit to the skin beyond that which is supplied by the skin's natural defense components. This process could also be used to compare the impacts from multiple products against one another as well as compare one or more of the products to an untreated area of skin.

Adhesive

As noted above, a skin sample may be taken with an adhesive. The adhesive can be, for example, in the form of a strip, patch, disc, or any other shape desired for the testing. The adhesive can have a backing. The adhesive can also be double sided to allow, for example, the adhesive with a skin sample to be stuck to another surface for testing. For example, the side of the adhesive not containing the skin sample could be adhered to a slide. Such adhesive or tape materials can include, without limitation, adhesive tapes such as D-SQUAME®, SEBUTAPE® (CuDerm Corporation, Dallas, Tex.), BLENDERM®, SCOTCHTAPE® (3M® Company, St. Paul, Minn.), patchProtect™ skin patch, hydrogels such as HYPAN® (Hymedix International, Inc., Dayton, N.J.), and other types of materials with adhesive properties or appropriate stickiness, such as glues, gums, and resins, and combinations thereof.

The adhesive is placed on the target skin surface. This can be, for example, the forearm, shin, forehead, and/or back, but any desired skin surface can be sampled. The adhesive is left in place for a sufficient amount of time to allow for attachment to the target skin surface. This can be, for example 5 seconds, 7 seconds, 10 seconds, 20 second, 25 seconds, 30 seconds, etc. This can be adjusted as needed for a particular test. In addition, pressure can be applied to the adhesive while on the skin to allow for better and/or more uniform adhesion. This can be done, for example, by pushing down on the adhesive while in contact with the skin, utilizing a roller to press the adhesive onto the skin, etc.

Once a sufficient amount of time has passed, the adhesive is peeled away from the skin. This can be done, for example, with fingers, tweezers, tongs, etc. The adhesive can be peeled, for example, starting at one edge and gently pulling the adhesive back and away from the skin surface.

Skin Sample Testing

Once the adhesive has been removed from the skin, it contains a skin sample. The skin sample on the adhesive can be placed on another surface, for example, a slide or an agar plate. The portion of the adhesive with the skin sample can be applied face up or face down depending on the desire of the tester. For example, a skin sample taken on an adhesive that is double sided can be adhered to a glass slide so that the skin sample containing portion is face up and the slide can be viewed under a microscope. In another example, the adhesive is placed on a trypticase soy agar plate with the skin sample side up. In addition, a skin sample can be quantified by absorption spectrometry, like D-Squame® Scan 850A.

The skin sample can then be tested. For example, a pH of the skin sample can be taken. This can be done, for example, by pH flat surface electrodes being placed on the skin.

A sample can also be treated while on the adhesive. This can include, for example, inoculation of the skin sample with a bacteria, fungus, or combination thereof. The materials for inoculation can be chosen based on the type of antimicrobial and/or antifungal properties of interest. These can include, for example, *Staphylococcus aureus, Escherichia coli, Klebsiella pneumoniae, Salmonella typhimurium, Candida albicans, Malassezia furfur*, or combinations thereof.

The sample can be treated by placing the desired material onto the skin sample containing side of the adhesive. For example, an adhesive can be inoculated by placing an aliquot of *Staphylococcus aureus* onto the skin sample. The inoculated adhesive can then be further processed or evaluated. In the case of inoculation, the inoculated sample may be spread on the strip utilizing an inoculation loop, allowed to air dry, placed in a humidifier, etc. until time to collect data.

An inoculated sample may be reviewed for the growth of a bacteria and/or fungus over time. This can be done, for example, utilizing an optical detection method, like the Soleris® system. In this type of system, the skin sample containing adhesive is placed into a liquid broth. As the microorganisms grow and metabolize nutrients, the optical assay monitors pH and other biochemical reactions that are taking place. The reagents used change their spectral patterns as the microorganisms grow. The changes can be detected optically, photometrically, by the instrument, at predetermined time intervals.

For each sample, the detection time (DT) will be recorded by the instrument. The DT is inversely proportional to the number and/or metabolic health of bacteria carried over on the adhesive. The longer DTs are indicative of a strong antibacterial effect while shorter DTs suggest a weak or no antibacterial effect. One can load germs with known loads (CFUs) onto an adhesive to generate a correlation curve with DTs. Then, germ load (CFU) on test tapes can be calculated by the standard curves. Further, germ efficacy comparisons like LOG reduction and germ inhibition rate (%) can also be calculated.

An inoculated sample can also be evaluated utilizing isothermal microcalorimetry. This is a method for looking at real time data of biological processes. For isothermal microcalorimetry, the skin sample containing adhesive is inoculated with the desired material. The inoculated adhesive is then placed into an ampule. The ampule is sealed, for example, with a crimper, and the ampule can be wiped to remove any potential contaminates from the exterior of the ampule. The ampule is then placed in an apparatus which can keep it at a constant predetermined temperature, chosen as appropriate for the materials being tested. For microorganism testing, the principle used to select temperature can be to utilize the temperature which will produce the fastest growth rate for the targeted microorganism. The temperature can be set, for example, in the range of about 15° C. to about 150° C. The set temperature can be, for example, 32° C., 35° C., or 37° C. The apparatus is capable of measuring and recording vs. elapsed time the net rate of heat flow (μJ/sec=μW) to or from the specimen ampule, and the cumulative amount of heat (J) consumed or produced. From this information, microbial growth parameters within the sample can be determined. This measurement method can allow an increased sensitivity in quantification of commensal microorganisms and exogenous microorganisms present on the adhesive.

Product Testing

A skin sample on an adhesive can be utilized for product testing. A skin sample on an adhesive can be taken as noted above. The sample may be utilized to determine the health of the skin and/or skin microbiome prior to any product application. This can be done utilizing the above test methods or other known test methods for determining such properties. These properties can be used as a control in product testing. In addition, multiple products can be tested against one another and/or compared to a control with respect to a particular attribute.

When testing a product, the target area of skin for testing can first be subjected to a wash out period. This is where a subject or subjects are given a specific cleanser to use on the skin for a specified amount of time prior to beginning a study. A wash out is generally utilized so that the skin of each subject has been subjected to the same treatment prior to product testing and thus, effects from other products can be ruled out as contributing to the results. A wash out period can also include a non-washing period meaning a subject may be asked to not cleanse the skin for a certain period of time. Also, during a wash out period, a subject may be asked to not use any products on the skin other than what has been supplied for the test. A wash out period will typically be at least 1 day and can last up to 10 days.

Once any requested wash out period is complete, a baseline skin sample can be taken from a target area. After any desired baseline sample is taken, a subject will start using a target product. The product may be a rinse-off product like, for example, a bar soap, liquid hand soap, facial cleanser, body wash, etc. The product may also be a leave-on product like, for example, a hand sanitizer, facial moisturizer, body lotion, etc. For a rinse-off product the protocol can include, for example, a water temperature, water hardness, flow rate, target area of skin to be washed, handling of the product sample, how to apply the sample to the skin, how to wash the skin with the sample, how much of the product to use, how long to wash with the product, how long to rinse after use of the product, if/how to dry the treated area of the arm after rinsing, how many times to repeat the process, how long to wait after application before a skin sample is taken, or varying combinations thereof. Once this process is complete, a skin sample can be taken with an adhesive as described above. This sample can then be treated (or not) and utilized to determine the target attribute, as also described above.

For a leave-on product a protocol can include, for example, a target area of skin on which the product is to be applied, handling of the product sample, how to apply the sample to the skin, how much of the product to use, how long to apply the product to the skin, how many times to repeat the process, how long to wait after application for taking a skin sample, or varying combinations thereof. Once this process is complete, a skin sample can be taken with an adhesive as described above. This sample can then be treated (or not) and utilized to determine the target attribute, as also described above.

Combinations

Here are some exemplary combinations within the scope of the invention.

A) A method for testing a skin sample, comprising: i) obtaining a sample of skin cells from a target area, wherein the skin cells are obtained with the application and removal of an adhesive; ii) applying a bacterial load, fungal load, viral load, or combination thereof, to the sample on the adhesive; and iii) measuring a bacterial level, fungal level, viral level, or a combination thereof, of the sample.

B) The method of paragraph A, wherein the adhesive comprises a tape strip, patch, or disc.

C) The method of any of paragraphs A or B, wherein the bacterial level, fungal level, viral level, or a combination thereof, is measured while the sample is on the adhesive.

D) The method of any of paragraphs A to D, wherein the bacterial level, fungal level, viral level, or a combination thereof, is measured via an optical detection system.

E) The method of paragraph D, wherein the sample is placed into a container containing a liquid growth medium for use during the optical detection of the bacterial level, fungal level, viral level, or a combination thereof.

F) The method of any of paragraphs A to D, wherein multiple samples are taken from the target area.

G) The method of any of paragraphs A to F, wherein the bacterial load comprises *Staphylococcus aureus, Escherichia coli, Klebsiella pneumoniae, Salmonella typhimurium*, or a combination thereof; preferably *Staphylococcus aureus*.

H) The method of any of paragraphs A to G, wherein the fungal load comprises *Candida albicans, Malassezia furfur*, or a combination thereof.

I) The method of any of paragraphs A to H, wherein the viral load comprises polio virus type 1, adeno virus type 5, influenza virus, or a combination thereof; preferably polio virus type 1.

J) The method of any of paragraphs A to I, wherein the bacterial level, fungal level, viral level, or a combination thereof, is utilized to determine the antibacterial, antiviral, and/or antifungal property of the skin sample.

K) The method of any of paragraphs A to I, wherein the target area is prepared prior to obtaining the skin sample.

L) The method of paragraph K, wherein the skin is prepared by washing the target area with a skin cleanser and rinsing the target area one or more times a day, preferably 3 times a day.

M) The method of paragraph L, wherein the prepping further comprises drying the target area after each cleanse and rinse combination.

N) The method of any of paragraphs L or M, wherein there is a one hour period between each cleansing and rinsing cycle.

O) Use of an inoculated skin sample on an adhesive for measuring an antimicrobial property, antifungal property, antiviral property, or a combination thereof of the skin sample, wherein the adhesive is preferably a tape strip.

P) The use of paragraph O, wherein the measurement is conducted while the skin sample is on the adhesive.

Q) A method for testing a skin product, comprising: applying a skin product to a target area; optionally, rinsing the skin product from the target area; obtaining a sample of skin cells from the target area, wherein the skin cells are obtained with the application and removal of an adhesive; applying a bacterial load, fungal load, viral load, or a combination thereof, to the sample on the adhesive; and measuring a bacterial level, fungal level, viral level, or a combination thereof, of the sample.

R) The method of paragraph Q, wherein the adhesive comprises a tape strip, patch, or disc.

S) The method of any of paragraphs Q or R, wherein the bacterial level, fungal level, viral level, or a combination thereof, is measured while the sample is on the adhesive.

T) The method of any of paragraphs Q to S, wherein the bacterial level, fungal level, or combination thereof, is measured over a predetermined amount of time.

U) The method of any of paragraphs Q to T, wherein the bacterial level, fungal level, viral level, or a combination thereof, is measured via an optical detection system.

V) The method of paragraph U, wherein the sample is placed into a container containing a liquid growth medium for use during the optical detection of the bacterial level, fungal level, viral level, or a combination thereof.

W) The method of any of paragraphs Q to V, wherein the bacterial level, fungal level, viral level, or a combination thereof, is utilized to determine the antibacterial, antiviral, and/or antifungal property of the skin product.

X) The method of any of paragraphs Q to X, wherein the bacterial level, fungal level, or the combination thereof is utilized to determine the efficacy of the skin product versus a second skin product.

Y) The method of any of paragraphs Q to X, wherein multiple samples are taken from the target area.

Z) The method of any of paragraphs Q to Y, wherein the bacterial load comprises *Staphylococcus aureus, Escherichia coli, Klebsiella pneumoniae, Salmonella typhimurium*, or a combination thereof; preferably *Staphylococcus aureus*.

AA) The method of any of paragraphs Q to Z, wherein the fungal load comprises *Candida albicans, Malassezia furfur*, or a combination thereof.

BB) The method of any of paragraphs Q to AA, wherein the viral load comprises polio virus type 1, adeno virus type 5, influenza virus, or a combination thereof; preferably polio virus type 1.

CC) The method of any of paragraphs Q to BB, wherein the target area is prepared prior to obtaining the skin sample.

DD) The method of any of paragraphs Q to CC, wherein the skin product comprises a soap, body wash, hand wash, facial cleanser, or intimate wash, and is applied to and rinsed from the skin one or more times a day, preferably 3 times a day.

EE) The method of paragraph DD, wherein the target site is dried after each cleanse and rinse combination.

FF) The method of any of paragraphs DD or EE, wherein there is a one hour period between each cleansing and rinsing cycle.

GG) The method of any of paragraphs Q to CC, wherein the skin product is a leave-on skin product.

HH) The method of paragraph GG, wherein the leave-on skin product is a hand sanitizer or moisturizer.

II) A method for comparing two skin products, comprising: i) applying one skin product to a target area; ii) optionally, rinsing the skin product from the target area; iii) obtaining a first sample of skin cells from the target area, wherein the skin cells are obtained with the application and removal of an adhesive; iv) applying a bacterial load, fungal load, viral load, or combination thereof, to the first sample while on the adhesive; v) measuring a bacterial level, fungal level, viral level, or a combination thereof, of the first sample; vi) applying a second skin product to a second target area; vii) optionally, rinsing the second skin product from the second target area; viii) obtaining a second sample of skin cells from the second target area, wherein the skin cells are obtained with the application and removal of an adhesive; ix) applying a bacterial load, fungal load, viral load, or a combination thereof, to the second sample while on the adhesive; x) measuring a bacterial level, fungal level, viral level, or a combination thereof, of the second sample; and xi) comparing the bacterial level, fungal level, viral level, or combination thereof of the first sample to the bacterial level, fungal level, viral level, or combination thereof of the second sample to determine the efficacy of the first product versus the second product.

EXAMPLES

1) Exemplary Method for Measuring Residual Antimicrobial Efficacy of a Product

This protocol provides a non-invasive method for evaluating the residual antimicrobe efficacy of a rinse-off product e.g. liquid hand soap, body wash product, bar soap, etc. against designated bacteria and fungi. The method includes in vivo product application, skin stratum corneum sampling via tape stripping, germ challenge test on skin samples on the tape strip, and germ load quantification via Soleris® Detection time (DT).

The test organism choice is based on the intended use of the results, for example, for advertising claim support. Two examples of bacteria that can be tested include *S. aureus* (ATCC® 6538/ATCC® 27127) and *E. coli* (ATCC® 10536). Ideally, the strain is within 5 generations and has a routine identification at a frequency as makes sense for the bacteria and the test.

The test organism is prepared for the study. For *S. aureus* and *E. coli*, if needed, refresh the test organism by streaking on a trypticase soy agar (TSA) plate and growing 18-24 hrs. On the second day, inoculate 1 colony of organism in a 50 ml tube containing 30 ml trypticase soy broth (TSB), and grow at 35±2° C. for 18 hours±15 min. On the test day, dilute the above bacteria culture by 1:10 or other concentrations to new TSB (e.g. 0.5 ml culture to 4.5 ml TSB media). The test organism can also be prepared with nutrient-limited mediums or buffers (e.g. 1:100 diluted TSB, nutrient buffer, and/or glycerol). The test organism culture may be used within half an hour for inoculating tape strips for all samples tested.

A target demographic is selected for testing, for example healthy Chinese individuals ages 20-60 inclusive with an even age distribution between 20-40 and 40-60. The subjects can be instructed to have a wash out period. For example, the wash out period can be to wash with a prescribed soap for days 1-5, shower on day 6 with city water only, and to refrain from taking a shower on day 7.

After the wash out period, a baseline skin sample may be taken on the target site prior to any product application. Then, the subjects are either instructed on how to do the following steps or a trained professional may do the steps on the subject. Utilizing tap water with a temperature of 35° C.+/−2° C. and a water flow rate of 4.0 L/min+/−0.3 L/min wet the volar surface of the forearm under the running water. If utilizing a solid soap, like a bar soap, briefly wet the soap under the running water. Then, rub the bar on the forearm, using an up-and-down motion from the wrist to the elbow, for 15 seconds. For liquid products, add 0.7 ml on forearm and spread evenly for 15 seconds. If necessary, set the bar down, continue to rub the lather on the forearm using the same up-and-down motion from the wrist to the elbow, for an additional 45 seconds. Rinse the forearm for 15 seconds by holding the arm under the running water. Do not rub the arm during rinsing. Remove the arm from the running water. Pat the arm dry with a paper towel without rubbing. The site is now ready for skin sampling with an adhesive. In the alternative, the above steps can be repeated so that the area is washed multiple times before sampling.

Once the target site, here the arm, is ready for sampling, which can be after the third wash on the third day of washing, a strip of adhesive tape is adhered to the skin site of interest avoiding folds. The skin site of interest can be marked in advance for consistency. To keep uniform pressure and reach optimal adhesive bond, a roller can be used to press the tape onto the skin surface (ex. twice on each site). Then, the tapes were peeled off from the skin and placed on the surface of a TSA agar plate with the skin sample side up. The tape strips can also be inoculated prior to being placed on the TSA agar plate.

A) Prepping and Testing with an Optical Detection Method (Ex. Soleris®)

Inoculate 10 µl of the tested microorganism culture on the skin sample side of each tape strip. Spread evenly over the tape surface, for example, with a sterile inoculation loop or pipette tip. Use one inoculation loop or pipette tip for each tape strip, and discard inoculation loop or pipette tip after use. Allow the inoculum to visually dry on the surface of the tape strip (approximately ~3-5 minutes).

The inoculated test strips can then be prepped for sampling measurement depending on what is intended to be measured. For example, if the inoculated test strips are going to be run through an optical analysis for detection of microbial growth and/or pH, then the inoculated tape strip residing on the TSA agar plate is placed into a humidified incubator at 35° C. and 60%±20% relative humidity until time of collection.

At each sampling time, aseptically transfer each tape into one NF-TVC (non-fermenting total viable count) vial for continuous monitoring for 24 hours to determine the detection times (DTs). Soleris parameters can be set as: Temperature 34° C.; Threshold: 10; Shuteye: 25; Skip 1.

B) Inoculation and Testing Using Isothermal Microcalorimetry

A tryptic soy broth (TSB)/Tween®80 (polyoxyethylenated sorbitan ester) solution is made. Tween®80 is added to generate a 0.1% solution. If only the commensals (bacteria already present on skin) are of interest, the inoculate is applied to the strip and carefully spread using, for example, an inoculation loop to cover the strip. Various volumes were can be used, for example, between 10 and 50 µL.

If *S. aureus* and/or *E. coli* is desired as part of testing on the strip, first dilutions should occur to generate the correct strength solution. Stock *S. aureus* and/or *E. coli* is diluted 1:9 into TSB, the first dilution generates a solution of $10^7$ cfu. This solution is then spread onto the strips, as above. The strips are then placed on a TSA agar plate with the skin sample side up. The TSA agar plates with strips on the surface were left to dry in a laminar flow cabinet, generally between 30 minutes and 2 hours depending on the amount of solution applied to each strip.

Once the strip is dry it can be tested. Agar from a TSA plate is cut into small cubes and 2 or 3 of these are placed into the bottom of the ampule that will contain a strip. The agar is used as a source of moisture within the ampule, as without it the bacteria may not grow. The strip is then put into the ampule. If the full strip is being used it can be carefully pushed into the ampule using tweezers, a funnel shape is often the end shape of the strip. If a thin section of the strip is being used, it can be dropped into the neck of the ampule using tweezers. The ampule is sealed with a crimper and the ampule is wiped with a paper towel to remove any potential moisture or oils on the external surface. The crimped ampule is loaded into an isothermal microcalorimetry machine (IMC).

The isothermal microcalorimetry machine is set to the temperature which produces the fastest growth rate for the target organism, for example, 37° C. A baseline reading is taken before the ampules are placed into the IMC. The IMC performs an equilibration phase before recording data. A baseline is recorded at the end of the run. The data is collected. The heat flow of the ampules can be plotted and used to determine bacterial growth. Runs can take 1 or more days.

2) Testing of a Rinse-Off Product

Figure 4:
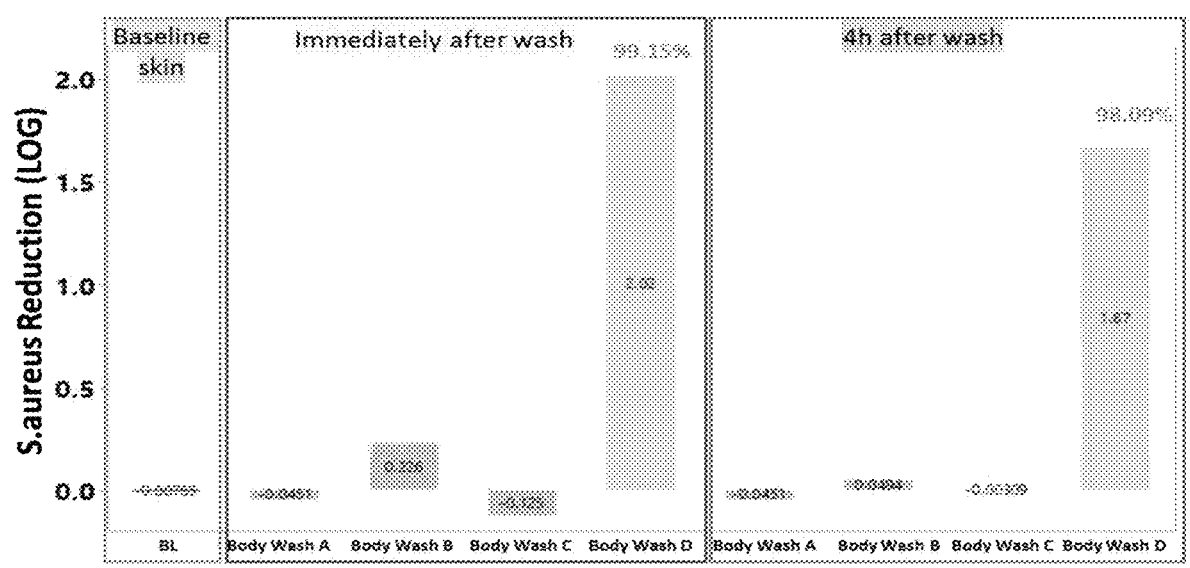
FIG. 4 is a graph depicting the impact of different body wash formulas on the efficacy of the skin's natural defense utilizing a skin sample on a tape strip which is inoculated directly on the tape strip.

A group of subjects were recruited for a study. The method of study used here is the same as that listed above for Example 1 including the Soleris® detection laid out in Example 1 (A). Test samples are taken with the adhesive immediately after the third wash on the third day of washing and again at 4 hours after the initial sample is taken. For the 4 hour sample, the panelist is requested to keep the portion of the arm being tested from making contact with anything. As can be seen in FIG. 4, the NET method is successfully utilized to understand the impact of varying body wash products on the sampled portion of skin's natural defense abilities. Here, Body Wash D showed a very strong enhancement of the skin's natural defense of *Staphylococcus aureus* where the skin's natural defense is represented as BL for baseline.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for evaluating a skin product, comprising the following steps in order:
   (a) preparing a target area on a healthy human subject by washing the target area with a skin cleanser and rinsing the target area one or more times per day for at least one day;
   (b) applying a skin product to the target area; optionally, rinsing the skin product from the target area;
   (c) obtaining a sample of skin cells from the target area, wherein the skin cells are obtained with the application and removal of an adhesive;
   (d) applying a bacterial load, fungal load, viral load, or combination thereof, to the sample on the adhesive;
   (e) measuring a bacterial level, fungal level, viral level, or a combination thereof, of the sample; and
   (f) evaluating the performance of the skin product.

2. The method of claim 1, wherein the adhesive comprises a tape strip, patch, or disc.

3. The method of claim 1, wherein the bacterial level, fungal level, viral level, or a combination thereof is measured while the sample is on the adhesive.

4. The method of claim 1, wherein the bacterial level, fungal level, viral level, or a combination thereof, is measured via an optical detection system.

5. The method of claim 4, wherein the sample is placed into a container containing a liquid growth medium for use during the optical detection of the bacterial level, fungal level, viral level, or a combination thereof.

6. The method of claim 1, wherein multiple samples are taken from the target area.

7. The method of claim 1, wherein a bacterial load is applied and the bacterial load is chosen from *Staphylococcus aureus, Escherichia coli, Klebsiella pneumoniae, Salmonella typhimurium*, or mixtures thereof.

8. The method of claim 7, wherein the bacterial load comprises *Staphylococcus aureus*.

9. The method of claim 1, wherein the fungal load is applied and the fungal load is chosen from *Candida albicans, Malassezia furfur*, or mixtures thereof.

10. The method of claim 1, wherein the viral load is applied and the viral load is chosen from polio virus type 1, adeno virus type 5, influenza virus, or mixtures thereof.

11. The method of claim 10, wherein the viral load comprises polio virus type 1.

12. The method of claim 1, wherein the skin is prepared by washing the target area with a skin cleanser and rinsing the target area one or more times per day.

13. The method of claim 12, wherein the skin is prepared by washing the target area with a skin cleanser and rinsing the target area 3 times per day.

14. The method of claim 12, wherein the prepping further comprises drying the target area after each cleanse and rinse combination.

15. The method of claim 12, wherein there is a one-hour period between each cleansing and rinsing cycle.

16. The method of claim 1, wherein the skin product is chosen from a soap, body wash, hand wash, facial cleanser, intimate wash, or mixtures thereof and is applied to and rinsed from the skin one or more times a day.

17. The method of claim 1, wherein the skin product is a leave-on skin product chosen from a hand sanitizer, body lotion, facial moisturizer, or mixtures thereof.

* * * * *